(12) United States Patent
McCullough et al.

(10) Patent No.: US 8,288,508 B2
(45) Date of Patent: Oct. 16, 2012

(54) UNIVERSAL GRIGNARD METATHESIS POLYMERIZATION

(75) Inventors: Richard D. McCullough, Pittsburgh, PA (US); Mihaela C. Iovu, Dallas, TX (US); Itaru Osaka, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 11/849,229

(22) Filed: Aug. 31, 2007

(65) Prior Publication Data

US 2008/0146754 A1   Jun. 19, 2008

Related U.S. Application Data

(60) Provisional application No. 60/841,548, filed on Sep. 1, 2006.

(51) Int. Cl.
*C08G 61/00* (2006.01)
(52) U.S. Cl. ........................................ 528/397; 528/396
(58) Field of Classification Search .................. 528/396, 528/397
See application file for complete search history.

(56) References Cited

U.S. PATENT DOCUMENTS

| | | | |
|---|---|---|---|
| 4,508,639 A * | 4/1985 | Camps et al. .................. | 252/500 |
| 5,777,070 A | 7/1998 | Inbasekaran et al. | |
| 5,900,327 A | 5/1999 | Pei et al. | |
| 5,962,631 A | 10/1999 | Woo et al. | |
| 6,166,172 A | 12/2000 | McCullough et al. | |
| 6,362,310 B1 | 3/2002 | Woo et al. | |
| 6,602,974 B1 | 8/2003 | McCullough et al. | |
| 6,777,531 B2 | 8/2004 | Yasuda et al. | |
| 7,126,013 B2 * | 10/2006 | Heeney et al. .................. | 549/59 |
| 2005/0218532 A1 | 10/2005 | Knochel et al. | |
| 2006/0076050 A1 | 4/2006 | Williams et al. | |
| 2006/0078761 A1 | 4/2006 | Williams et al. | |
| 2006/0175582 A1 | 8/2006 | Hammond et al. | |

FOREIGN PATENT DOCUMENTS

| | | |
|---|---|---|
| EP | 1 028 136 A | 8/2000 |
| EP | 1 582 523 A | 10/2005 |
| EP | 1582523 A1 * | 10/2005 |
| JP | 2000-024613 | 1/2000 |
| WO | WO 03/001290 A | 1/2003 |
| WO | WO 2006/084545 A | 8/2006 |

OTHER PUBLICATIONS

Yamamoto et al. (Soluble Copolymers of p-Phenylene and m-Phenylene. Their Basic Properties. Chemistry Letters. 2000, p. 720-721).*
Sato et al. (Preparation and Properties of Poly(p-phenylene) and Polynaphthylene. Makromol. Chem. 1983, 85, 2241-2249).*
Miyakoshi et al. (Catalyst-Transfer Polycondensation for the Synthesis of Poly(p-phenylene) with Controlled Molecular Weight and Low Polydispersity. J. Am. Chem. Soc. 2006, 128, 16012-16013).*
McCullough et al. Grignard Metathesis Method (GRIM): Toward a Universal Method for the Synthesis of Conjugated Polymers. Macromolecules, 2009, 42, 30-32.*
Iraqi (Preparation of poly(9-alkylcarbazole-3,6-diyl)s via palladium catalysed cross-coupling reactions. Synthetic Metals, 2001, 119, pp. 159-160).*
Kovacic (Synthesis and Properties of Poly(1-phenyl 2,5-pyrrolylene) and poly(1-benzyl 2,5-pyrrolylene. Polymer Letters Edition, 1981, pp. 395-400).*
Wellinghoff (Synthesis and Characterization of Highly Conducting, Environmentally Stable, Iodine Complexes of a Soluble Poly N-Methyl 3,3' Carbazolyl. Journal De Physique, 1983, C3, Supplement 6, pp. 677-681).*
Rusanov (Polycondensation reactions catalysed by Ni and Pd complexes as the method for the synthesis of carbo- and hetero-cyclic polyarylenes. Russ. Chem. Rev., 1996, 65, pp. 785-795).*
CAPlus Abstract (AN 1986:573149), 1986, 1 page of Sato (Preparation and conductivity of polyarylenes. Kenkyu Hokoku-Sen'i Kobunshi Zairyo Kenkyuso, 1986, 150, pp. 27-32).*
Knochel (Highly Functionalized Organomagnesium Reagents Prepared through Halogen-Metal Exchange. Angew. Chem. Int. Ed. 2003, 42, 4302-2320).*
Awad et al., "Deprotonation of chloropyridines using lithium magnesates", Tetrahedron Lett., vol. 45, No. 42, pp. 7873-7877 (2004).
Boymond et al., "Preparation of Highly Functionalized Grignard Reagents by an Iodine—Magnesium Exchange Reaction and its Application in Solid-Phase Synthesis", Agnew. Chem. Int. Ed., Comm., vol. 37, No. 12, pp. 1701-1703 (1998).
Carter et al., "Nickel(0)-Mediated Coupling Polymerizations via Microwave-Assisted Chemistry", Macromolecules, vol. 35, pp. 6757-6759 (2002).
Dolman et al., "Selective metal-halogen exchange of 4,4'-dibromobiphenyl mediated by lithium tributylmagnesiate", Tetrahedron, vol. 62, No. 21, pp. 5092-5098 (Apr. 2006).
Ewbank et al., "Regioregular poly(thiophene-3-alkanoic acid)s: water soluble conducting polymers suitable for chromatic chemosensing in solution and solid state", Tetrahedron, vol. 60, pp. 11269-11275 (2004).
Greene & Greene, *Protective Groups in Organic Synthesis*, John Wiley (Table of Contents) (4 pages) (1981).

(Continued)

*Primary Examiner* — Ling Choi
*Assistant Examiner* — Brieann R Fink
(74) *Attorney, Agent, or Firm* — Foley & Lardner LLP

(57) ABSTRACT

Universal Grignard Metathesis (GRIM) reactions which provide access to conjugated polymers by GRIM methods. A method comprising: providing an unsaturated ring compound comprising at least two halogen ring substituents, providing an organomagnesium reagent comprising an organomagnesium component and a metal activation agent, combining the unsaturated ring compound with the reagent to form a second compound by metal-halogen exchange, wherein the metal activation agent activates the metal-halogen exchange, coupling the second compound to itself in an oligomerization or polymerization reaction. Metal activation agent can be lithium chloride. The process is commercially attractive and can be executed in good yields. Polyfluorenes, polypyrroles, and polythiophenes can be prepared for use in OLED, PLED, photovoltaic, transistor, antistatic coatings, and sensor applications.

27 Claims, 14 Drawing Sheets

OTHER PUBLICATIONS

Herguth et al., "Highly Efficient Fluorene- and Benzothiadiazole-Based Conjugated Copolymers for Polymer Light-Emitting Diodes", Macromolecules, vol. 35, pp. 6094-6100 (2002).

Hwang et al., "Conjugated Polymers Based on Phenothiazine and Fluorene in Light-Emitting Diodes and Field Effect Transistors", Chem. Mater., vol. 16, pp. 1298-1303 (2004).

Iida et al. "Tributylmagnesiumate complex-mediated novel bromine-magnesium exchange reaction for selective monosubstituion of dibromoarenes", Tetrahedron Lett., vol. 42, pp. 4841-4844 (2001).

Inoue et al., "Selective Halogen-Magnesium Exchange Reaction via Organomagnesium Ate Complex", J. Org. Chem., vol. 66, pp. 4333-4339 (2001).

Iovu et al., "Grignard Metathesis (GRIM) Method for the Synthesis of Regioregular Poly(3-Alkylthiophenes) with Well-Defined Molecular Weights", Polymer Preprints, vol. 46, No. 1, pp. 660-661 (2005).

Kameshima et al., "Synthesis and Properties of Fluorene-Based Fluorinated Polymers", J. Polymer Sci., Polym. Chem., vol. 39, pp. 3143-3150 (2001).

Kappaun et al., "Preparation of Poly(fluorene)s Using *trans*-Bis(dicyclohexylamine)palladium Diacetate as a Catalyst: Scope and Limitations", J. Polym. Sci., Polym. Chem., vol. 44, pp. 2130-2138 (2006).

Killian et al., "Living Polymerizaton of α-Olefins Using $Ni^{II}13$ α-Diimine Catalysts. Synthesis of New Block Polymers Based on α-Olefins", J. Am. Chem. Soc., vol. 118, pp. 11664-11665 (1996).

Kitagawa et al, "Halogen-Magnesium Exchange via Trialkylmagnesates for the Preparation of Aryl- and Alkenylmagnesium Reagents", Angew. Chem. Int. Ed., vol. 39, pp. 2481-2483 (2000).

Li et al., "Synthesis and Properties of Random and Alternating Fluorene/Carbazole Copolymers for Use in Blue Light-Emitting Devices", Chem. Mater., vol. 16, pp. 2165-2173 (2004).

Liu et al., "Employing MALDI-MS on Poly(alkylthiophenes): Analysis of Molecular Weights, Molecular Weight Distributions, End Group Structures, and End-Group Modifications", Macromolecules, vol. 32, pp. 5777-5785 (1999).

Liu et al., "Synthesis, Characterization, and Structure-Property Relationship of Novel Fluorene-Thiophene-Based Conjugated Copolymers", Macromolecules, vol. 33, pp. 8945-8952 (2000).

Loewe et al., "A Simple Method to Prepare Head-to-Tail Coupled, Regioregular Poly(3-alkylthiophenes) Using Grignard Metathesis", Adv. Mater., vol. 11, No. 3, pp. 250-253 (1999).

Loewe et al., "Regioregular, Head-to-Tail Coupled Poly(3-alkylthiophenes) Made Easy by the GRIM Method: Investigation of the Reaction and the Origin of Regioselectivity", Macromolecules, vol. 34, pp. 4324-4333 (2001).

Marsitzky et al, "Poly-2,8-(indenofluorene-*co*-anthracene)—A Colorfast Blue-Light-Emitting Random Copolymer", Adv. Mater., vol. 13, No. 14, pp. 1096-1099 (2001).

Pasini et al., "Electroluminescent poly(fluorene-*co*-thiophene-S,S-dioxide): synthesis, characterization and structure-property relationships", J. Mater. Chem., vol. 13, pp. 807-813 (2003).

Pei et al., "Efficient Photoluminescence and Electroluminescence from a Soluble Polyfluorene", J. Am. Chem. Soc., vol. 118, pp. 7416-7417 (1996).

Peng et al., "Synthesis and Electroluminescent Properties of Copolymers Based on Fluorene and 2,5-Di(2-hexyloxyphenyl)thiazolothiazole", Macromolecules, vol. 38, pp. 7292-7298 (Jul. 2005).

Ranger et al., "New Well-Defined Poly(2,7-Fluorene) Derivatives: Photoluminescence and Base Doping", Macromolecules, vol. 30, pp. 7686-7691 (1997).

Sheina et al., "Chain Growth Mechanism for Regioregular Nickel-Initiated Cross-Coupling Polymerizations", Macromolecules, vol. 37, pp. 3526-3528 (2004).

Tsuie et al., "Electroactive and luminescent polymers: new fluorene-heterocycle-based hybrids", J. Mater. Chem., vol. 9, pp. 2189-2200 (1999).

Wakefield, B. J., *Organomagnesiuim Methods in Organic Synthesis*, Academic Press: New York (Table of Contents) (6 pages) (1995).

Zhai et al., "Regioregular polythiophene/gold nanoparticle hybrid materials", J. Mater. Chem., vol. 14, pp. 141-143 (2004).

Zhai et al., "A Simple Method to Generate Side-Chain Derivatives of Regioregular Polythiophene via the GRIM Metathesis and Post-polymerization Functionalization", Macromolecules, vol. 36, pp. 61-64 (2003).

Zhai et al., "Soft-Lithography Patterning of Functionalized Regioregular Polythiophenes", Langmuir, vol. 19, pp. 6492-6497 (2003).

PCT/US2007/077461 filed Aug. 31, 2007, Intl. Search Report dated Dec. 27, 2007 (4 pages).

Stefan et al., "Grignard Metathesis Method (GRIM): Toward a Universal Method for the Synthesis of Conjugated Polymers", Macromolecules, vol. 42, pp. 30-32 (2009).

* cited by examiner

Ni(dppp)Cl$_2$

Ni(dppb)Cl$_2$

UNIVERSAL GRIGNARD METATHESIS POLYMERIZATION

RELATED APPLICATIONS

This application claims the benefit of U.S. Provisional Application Ser. No. 60/841,548, filed Sep. 1, 2006, which is incorporated herein by reference in its entirety.

FEDERAL FUNDING STATEMENT

One or more embodiments described herein were developed with federal funding under grant numbers National Science Foundation, CHE 0415369.

BACKGROUND

A need exists to find better methods to make oligomers and polymers from monomers. For example, some polymerization methods may work better for some monomers compared to other monomers. To the extent the polymerization method is limited, then commercial applications of the polymers are limited because in many cases the precise properties of the polymers need to be tailored for a particular application. Fine tailoring of polymer properties can be achieved by fine-tuning the structures of the monomers and polymers. This fine tuning includes, for example, microstructure and regioregularity considerations.

In particular, a need exists to develop better polymerization methods for making conducting polymers, or polymers having conjugated backbones. These include for example polythiophene, polyphenylene, polyacetylene, poly(phenylene vinylene), polyaniline, polypyrrole, polyfluorene, and derivatives thereof. These polymers can be difficult to make because in many cases they may become insoluble, infusible, or difficult to process. They may also suffer from instability. Structural inhomogeneity can become a problem. In many cases, the polymers need to be doped before they can be used. Conducting polymers can be used in applications such as, for example, transistors, light emitting devices (OLEDs and PLEDs), solar cells, and sensors. A particularly important example of conducting polymer is the polythiophene family, which includes homopolymers, copolymers, and block copolymers, see for example, U.S. Pat. No. 6,602,974 (Carnegie Mellon University). Also particularly important are polyfluorenes. See for example U.S. Pat. No. 5,900,327 (Uniax)

One example of a commercially useful synthesis of conducting polymer can be found in U.S. Pat. No. 6,166,172 to McCullough et al. (sometimes called the "GRIM" method). In particular, this method can be used to prepare regioregular polythiophenes (see for example FIG. 8 in the present application below). In this patent, use of organomagnesium reagents are described in the conversion of monomers to polymers using metal-halogen exchange, including magnesium-bromine exchange. However, limits and slowness of magnesium-bromine exchange are known as noted in U.S. Patent Publication 2005/0218532 to Knochel et al. Organic iodides may not be possible because of lack of availability or expense. In the prior art, synthesis of polyfluorenes and other conducting polymers has been carried out by the Yamamoto methods and modified Suzuki methods. Difficulties in present methods are described in for example Kappaun et al., J. Polym. Sci., Polym. Chem., Vol. 44, 2130-2138 (2006).

A need exists to improve upon these methods, particularly in ways that facilitate commercialization.

SUMMARY

The various embodiments described herein are not limited by this summary section but can be for example, methods of making, compositions, devices, and methods of using. Because the prior art GRIM method is expanded as described in detail below, various embodiments described herein can be called "Universal GRIM" for convenience.

One embodiment provides a method comprising: providing an unsaturated ring compound comprising at least two halogen ring substituents, providing an organomagnesium reagent comprising an organomagnesium component and a metal activation agent, combining the unsaturated ring compound with the reagent to form a second compound by metal-halogen exchange, wherein the metal activation agent activates the metal-halogen exchange, and coupling the second compound to itself in an oligomerization or polymerization reaction.

Another embodiment provides a method comprising: providing an unsaturated ring compound comprising at least two halogen ring substituents, providing a reagent represented by $R^1(MgX)_n \cdot LiY$, combining the unsaturated ring compound with the reagent to form a second compound, and polymerizing the second compound, wherein for the reagent:

n is 1 or 2;

$R^1$ is a substituted or unsubstituted C4-C24 aryl or C3-C24 heteroaryl, containing one or more heteroatoms as B, O, N, S, Se, P, F, Cl, Br, I, or Si; linear or branched, substituted or unsubstituted C1-C20 alkyl, C2-C20 alkenyl or C2-C20 alkinyl; or substituted or unsubstituted C3-C20 cycloalkyl; or a derivative thereof;

X and Y are independently or both Cl, Br or I, preferably Cl; $HalO_n$ (where n=3, 4); carboxylate of formula $RCO_2$; alkoxide or phenoxide of formula RO; dialkoxide of formula LiO—R—O; disilazide of formula $(R_3Si)_2N$; thiolate of formula SR; $RP(O)O_2$; or SCOR; where R is defined as $R^1$ above;

linear or branched, substituted or unsubstituted C1-C20 alkyl or C3-C20 cycloalkyl amine of formula RNH; dialkyl/arylamine of formula $R_2N$ (where R is defined as above or $R_2N$ represents a heterocyclic alkylamine); phosphine of formula $PR_2$ (where R is defined as above or PR2 represents a heterocyclic phosphine); $O_nSR$ (where n=2 or 3 and R is defined as above); or $NO_n$ (where n=2 or 3); or $X=R^1$ as defined above; and a derivative thereof.

Another embodiment comprises a method comprising: providing a heterocyclic, aromatic, or biphenyl ring compound comprising two bromine ring substituents, providing an organomagnesium reagent comprising an organomagnesium component and a lithium activation agent, combining the ring compound with the organomagnesium reagent to form a second compound, polymerizing the second compound with transition metal complex to form a conjugated polymer.

Another embodiment provides a method comprising: providing a heterocyclic, aromatic, or biphenyl ring compound comprising two halogen ring substituents, providing a magnesium ate complex, combining the ring compound with the complex to form a second compound, polymerizing the second compound with transition metal complex to form a conjugated polymer.

Advantages which can be found in one or more embodiments described herein include high yields, fast reaction speeds, simple conditions, commercially available reagents, generally commercially attractive polymerization conditions, an expansion of the commercially attractive GRIM method to new and commercially important polymers, and new routes to blue light emitters.

DETAILED DESCRIPTION

Introduction

One embodiment provides a method comprising: providing an unsaturated ring compound comprising at least two halogen ring substituents, providing an organomagnesium reagent comprising an organomagnesium component and a metal activation agent, combining the unsaturated ring compound with the reagent to form a second compound by metal-halogen exchange, wherein the metal activation agent activates the metal-halogen exchange, and coupling the second compound to itself in an oligomerization or polymerization reaction.

Figure 1:
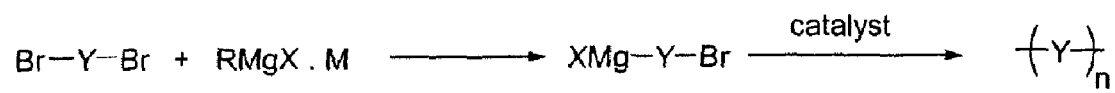
FIG. 1 illustrates an embodiment for the universal GRIM method for the synthesis of conducting polymers.

FIG. 1 illustrates a reaction scheme showing examples of the unsaturated ring compound (represented as Br—Y—Br) and the organomagnesium reagent (RMgX.M). Table 1 below illustrates examples of monomers and additives which can be used, and further description is provided below.

TABLE 1

Monomers and additives used for universal GRIM of aryl and heteroaryl halides

| Br—Y—Br | R' | M | Catalyst |
|---|---|---|---|
| 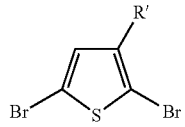 | Alkyl, alkoxyl | LiCl, tBuOLi, KBr, tBuOK MgCl$_2$, ZnCl$_2$ | Ni, Pd, Pt Ligands: phosphines, fluorophosphines, Diimine |
| 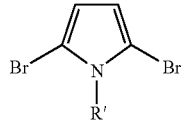 | Alkyl | LiCl, tBuOLi, KBr, tBuOK MgCl$_2$, ZnCl$_2$ | Ni, Pd, Pt Ligands: phosphines, fluorophosphines, Diimine |
| 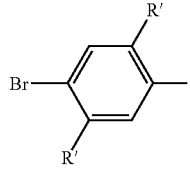 | Alkoxyl | LiCl, tBuOLi, KBr, tBuOK MgCl$_2$, ZnCl$_2$ | Ni, Pd, Pt Ligands: phosphines, fluorophosphines, Diimine |
| 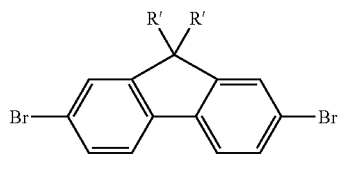 | Alkyl | LiCl, tBuOLi, KBr, tBuOK MgCl$_2$, ZnCl$_2$ | Ni, Pd, Pt Ligands: phosphines, fluorophosphines, Diimine |
| 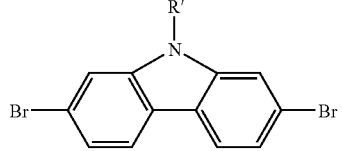 | Alkyl | LiCl, tBuOLi, KBr, tBuOK MgCl$_2$, ZnCl$_2$ | Ni, Pd, Pt Ligands: phosphines, fluorophosphines, Diimine |

The method can be used with unreactive aryl and heteroaryl halide monomers, generating polymers upon the addition of transition metal catalysts.

Metal Halogen Exchange

Figure 2:
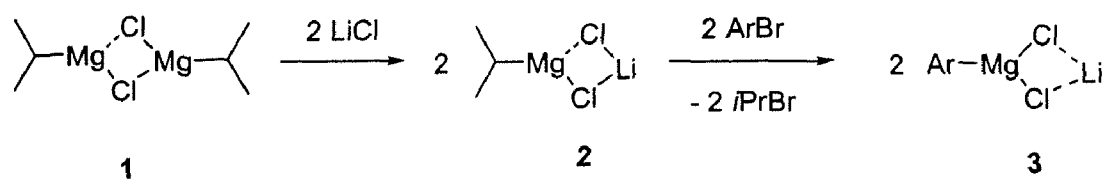
FIG. 2 illustrates catalysis of Br/Mg exchange reaction with lithium chloride
Figure 8:
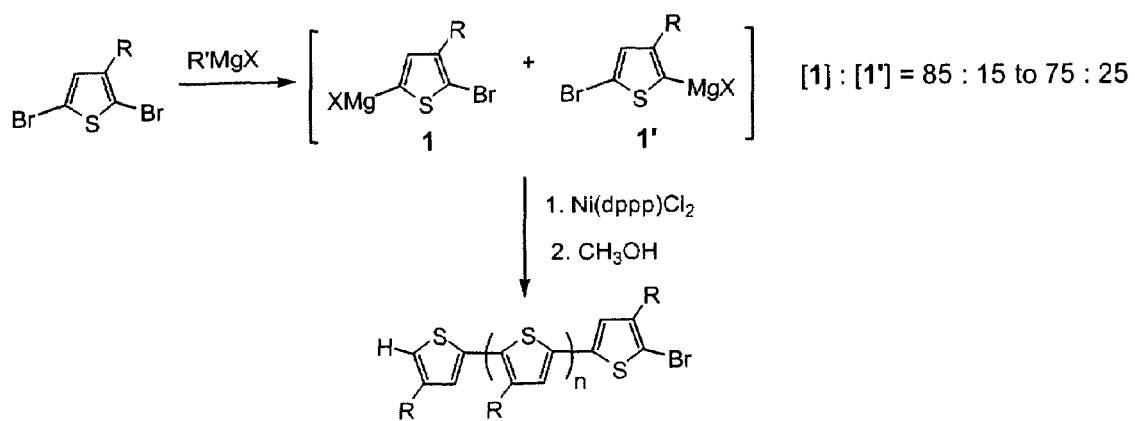
FIG. 8 illustrates synthesis of regioregular poly(3-alkylthiophenes) by the Grignard metathesis method (GRIM) including the metal halogen exchange process.

FIG. 2 (see also FIG. 8) illustrates principles of the organomagnesium reagent and the metal halogen exchange described herein in reaction with the unsaturated ring compound. Addition of lithium chloride to a Grignard reagent breaks the polymeric aggregates producing the reactive complex 3. While the present claims are not limited by theory, the magnesiate character of 3 may be responsible for the enhanced reactivity of this reagent. This magnesiate is expected to have higher reactivity toward electrophiles, such as nickel phosphine catalysts. Metal halogen exchange, in particular bromine-magnesium exchange, is known in the art. See for example Loewe et al., Macromolecules, 2001, 34, 4324-4333; Loewe et al., Adv. Mater., 1999, 11, No. 3, 250-253; U.S. Pat. No. 6,166,172; Knochel et al., Angew. Chem. Int. Ed., Communications, 1998, 37, No. 12, pages 1701-1703.

The metal halogen exchange reaction can be characterized by:

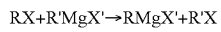

Reaction is between Grignard reagents and organic halides to form a new Grignard reagent. This reaction generally has been used less than counterpart organolithium reactions. However, the reaction can be used for aryl and heteroaryl bromides and iodides. Presently, the reaction is more broadly used in polymer chemistry than heretofore possible to form conjugated polymers.

Presently, a variety of conjugated polymers can be prepared by the methods herein including for example polyfluorenes, polypyrroles, poly(phenylenes), and polythiophenes, as well as derivatives, homopolymers, and copolymers thereof. Another example are the polycarbazoles including derivatives, homopolymers, and copolymers thereof.

The reaction should be fast enough to be commercially realistic. For example, without activation, some reactions may only provide 5-10% monomer conversion after 24-48 hours.

Unsaturated Ring Compound

A wide variety of unsaturated ring compounds can be used. In particular, unsaturated ring compounds can be used which are difficult to polymerize in the GRIM process heretofore known using unmodified or unactivated organomagnesium reagents. Certain aryl and heteroaryl halides for example are relatively unreactive in the magnesium halogen exchange process, which can prevent use of the GRIM method. In addition, unsaturated ring compounds can be used which are useful in the synthesis of conjugated polymers. They can provide multiple alternating single and double bonds which provide for extended conjugation, particular when monomer or dimer units are connected by carbon-carbon bonds during polymerization.

A variety of embodiment can be used. For example, the unsaturated ring compound can comprise at least one aromatic or pseudo-aromatic ring. The unsaturated ring compound can comprise one or two rings, wherein the rings are five or six membered rings. The unsaturated ring compound can be a heterocyclic ring compound. For example, the ring or rings can comprise all carbon atoms except for one heteroatom such as for example nitrogen or sulfur. Alternatively, the unsaturated ring compound can be a non-heterocyclic ring compound. The ring or rings can comprise all carbon atoms.

The unsaturated ring compound can comprise a single heterocyclic ring, a single aromatic ring, or a single bi-phenyl ring system.

The unsaturated ring compound can comprise two halogen atoms which are bonded to carbon ring atoms which are not adjacent to each other. For example, the carbon ring atoms can be separated from each other by a heteroatom such as sulfur or nitrogen, or by one or more carbon atoms. The unsaturated ring compound can comprise two rings, wherein each ring comprises a halogen ring substituent.

In particular, the unsaturated ring compound can be a thiophene compound, a pyrrole compound, or a fluorene compound. Other examples include a carbazole compound or a phenyl compound.

The unsaturated ring compound can comprise non-hydrogen substitutents such as for example alkyl, aryl, arylalkyl, or alkoxy substituents. These substituents can be directly bonded to the ring as ring substituents or can be bonded to an atom that is used to bridge two ring structures such as the two substituents shown the working examples below for the fluorene embodiment (9,9 substitution). For example, this can be represented by Ar1-B(R1)(R2)-Ar2 wherein R1 and R2 are non-hydrogen substituents, and B is a bridging moiety such as a —CH2-group bridging Ar1 and Ar2. The Ar1 and Ar2 can be further directly linked without a bridging moiety as in the fluorene embodiment. In addition, the substituent can be bonded to the ring heteroatom as in the pyrrole embodiment of the working examples. In a six membered aromatic ring, the substituents can be ortho, meta, or para to the halogen groups.

The ring substituents can comprise heteroatoms such as for example oxygen, nitrogen, or sulfur. They can comprise multiple heteroatoms such as for example alkyleneoxy groups. They can be electron withdrawing or electron releasing groups. In many cases, the function of these ring substitutents are to modify the properties of the resultant polymers such as for example solubility or band gap (which affects electronic and optical properties), as well as morphological properties such as crystallinity and glass transition temperature. Alkyl groups can be for example C1-C24, or C2-C18, or C3-C12 compounds including C1, C2, C3, C4, C5, C6, C7, C8, C9, C10, C11, and C12 groups. Examples include —(CH$_2$)5, —O(CH$_2$)$_5$, or —O(CH$_2$CH$_2$O)$_3$CH$_2$CH$_3$ and octyloxy. The unsaturated ring compound can comprise one, two, or more of these substituents, and if two or more are present, they can be the same or different.

Ring substituents can be fluorinated as described in for example Kameshima et al, J. Polymer Sci., Polym. Chem., Vol. 39, 3143-3150 (2001). If desired, protective groups can be used if a group is sensitive to metal halogen exchange processes. See for example, U.S. Pat. No. 6,166,172 and reference to Greene and Greene, "Protective Groups in Organic Synthesis," John Wiley, 1981.

The substituents are not particularly limited to the extent they can be used in the synthesis.

Halogen Ring Substituents

The halogens (-X) can function as leaving groups and sites for metal-halogen exchange. In one embodiment, two halogens are present. The at least two halogens can be the same or different halogens. Usually, however, only one of the halogens is primarily reactive in the metal halogen exchange. If the two halogens are present on the same ring, they can be para to each other. If they are present on a five membered heterocyclic ring such as thiophene or pyrrole, they can be in the 2,5 positions. In a fluorene, they can be in the 2,7 positions.

The halogen can be bromine, iodine, or chlorine. A preferred example is bromine, and both halogens can be bromine.

Organomagnesium Reagent

The organomagnesium reagent can be used as a single reagent but typically is provided by combining two components: an organomagnesium component and a metal activation component, which are described further below. The purpose of the organomagnesium reagent is to engage in metal-halogen exchange with the unsaturated ring compound comprising halogen ring substituents. Moreover, the resultant product should be able to undergo polymerization with itself in the presence of transition metal complex.

The organo group in the organomagnesium reagent, as described further below, can be for example alkyl, alkenyl, alkynyl, cycloalkyl, aryl, or heteroaryl, including linear, branched, and cyclic variations thereof.

The reagent can be represented by: $R^1(MgX)_n \cdot LiY$, as described in for example in US Patent Publication 2005/0218532 to Knochel et al., which is hereby incorporated by reference in its entirety including the structures and nomenclature of all reagents described therein, wherein n is 1 or 2;

$R^1$ is a substituted or unsubstituted C4-C24 aryl or C3-C24 heteroaryl, containing one or more heteroatoms as B, O, N, S, Se, P, F, Cl, Br, I, or Si; linear or branched, substituted or unsubstituted C1-C20 alkyl, C2-C20 alkenyl or C2-C20 alkinyl; or substituted or unsubstituted C3-C20 cycloalkyl; or a derivative thereof;

X and Y are independently or both Cl, Br or I, preferably Cl; $HalO_n$ (where n=3, 4); carboxylate of formula $RCO_2$; alkoxide or phenoxide of formula RO; dialkoxide of formula LiO—R—O; disilazide of formula $(R_3Si)_2N$; thiolate of formula SR; $RP(O)O_2$; or SCOR; where R is defined as $R^1$ above;

linear or branched, substituted or unsubstituted C1-C20 alkyl or C3-C20 cycloalkyl amine of formula RNH; dialkyl/arylamine of formula $R_2N$ (where R is defined as above or $R_2N$ represents a heterocyclic alkylamine); phosphine of formula $PR_2$ (where R is defined as above or PR2 represents a heterocyclic phosphine); $O_nSR$ (where n=2 or 3 and R is defined as above); or $NO_n$ (where n=2 or 3); or $X=R^1$ as defined above; and a derivative thereof.

In particular, the reagent can be represented by $R^1(MgX) \cdot LiY$ or $(R^1)_2(MgX) \cdot LiY$.

The reagent can be used in conjunction with solvents, one more additives, or solvents and one or more additives.

Solvents can be for example an inert aprotic solvent such as for example tetrahydrofuran, diethyl ether, 2-methylTHF, dibutyl ether, tert-butylmethyl ether, dimethoxy ethane, dioxane, triethylamine, pyridine, ethyldiisopropylamine, dichloromethane, 1,2-dichloroethane, dimethylsulfide, dibutylsulfide, benzene, toluene, xylene, pentane, hexane, or heptane, or combinations thereof. Solvent mixtures can be used. Solvents can be used that are useful for Grignard reactions.

The concentration of the organomagnesium reagent in solvent can be for example about 0.05 M to about 3 M. Increased concentration can be used until the compounds are no longer soluble.

In some cases, the organomagnesium reagent can be used as a solid without solvent.

Two general preparation methods can be used as illustrated below in the working examples. In a first method, a Grignard reagent is preformed from for example alkyl halide and magnesium, and then mixed with the metal activation agent such as lithium chloride. In a second method, no preformed Grignard reagent is made. Rather, magnesium metal, present in slight molar excess, can be mixed both with alkyl halide and with the metal activation agent such as lithium chloride.

An additional additive can be used to further enhance the metal halogen exchange reaction, particularly when the Grignard reagent is less reactive, such as for example polyether, polyamine, multidentate amines, crown ether, dioxanes, oligo- or polyethyleneglycol ethers, derivatives of urea, amides of formula $RCONR_2$ (where R is defined as for example an alkyl group or any other group that can be linked to an amide). In particular, dioxane and crown ether can be used.

The molar ratio between $R^1(MgX)_n$ and LiY can be for example about 0.05 to about 6.0.

In one combination, in particular, Y can be Cl and $R^1$ can be sec-butyl or isopropyl.

Organomagnesium reagent can be obtained commercially from Chemetall Gmbh (Frankfurt, Germany), Lithium Division, presently described under a "TurboGrignard" label.

Another embodiment is for use of magnesate complexes. For example, these can result from mixing of n-BuLi with n-BuMgCl or t-BuMgCl. See for example Iida et al., Tetrahedron Letters, 42 (2001) 4841-4844 including JP 2000-024613 cited in reference 7.

Organomagnesium Component

See for example Wakefield, B. J., Organomagnesium Methods in Organic Synthesis: Academic Press: New York, 1995.

The purpose of the organomagnesium component is to provide the magnesium for the metal-halogen exchange with the unsaturated ring compound and provide an organo component which does not interfere with and even promotes the metal halogen exchange. The organomagnesium component can comprise an aryl or alkyl magnesium reagent.

In the representation $R^1(MgX)_n \cdot LiY$ for the organomagnesium reagent, the organomagnesium component can be the $R^1(MgX)_n$ component.

Metal Activation Agent

The metal activation agent can comprise a metal such as for example lithium, magnesium, potassium, or zinc. The purpose of the metal activation agent is to activate the metal-halogen exchange, which can in turn also activate the coupling process. In other words, the organomagnesium reagent comprises a component which is a metal activation agent which activates the metal-halogen exchange. Activation can be determined by examining the reaction without the metal activation agent to see whether the reaction is slower at a particular temperature. One can by comparative testing determine whether the metal activation agents speeds up or otherwise enhances the reaction. In some cases, no reaction will be possible without the metal activation agent. In other cases, the reaction will be possible without the metal activation agent, but the rate of reaction will be much faster with the metal activation agent. In many cases, the speeding up of reaction can be the difference between a commercially viable process and a process which has only academic significance at best. For example, the speed of reaction can be at least doubled (2×), or at least tripled (3×), or at least quadrupled (4×), or at least 10×, or at least 50×, or at least 100×, or at least 1,000× faster. To the extent the reaction is considered an equilibrium, the reaction is shifted to the right with use of the metal activation agent. Both kinetic and thermodynamic aspects can be used to describe the metal activation agent impact on reaction.

The metal activation agent can comprise for example lithium compounds or salts, potassium compounds or salts, magnesium compounds or salts, and zinc compounds or salts, including for example lithium compounds, or lithium salts. Additional examples include LiCl, tBuOLi, KBr, tBuOK, $MgCl_2$, and $ZnCl_2$.

Organolithium compounds can be used including alkyllithium compounds and n-alkyllithium compound such as for example n-butyllithium. With reaction with a magnesium compound, these can form magnesium ate complexes such as, for example, n-$Bu_3$MgLi. These can be more reactive reagents in magnesium halogen exchange including those with general formula ($R_3$MgLi; R=for example, alkyl: n-butyl, t-butyl, isopropyl). The use of magnesium ate complexes for the magnesium halogen exchange allows reactions to be performed at low temperatures (e.g., below room temperature, including −30° C. to 0° C.) with shorter reaction times (Table 2 last entry). They can provide a yield of mono-reacted monomer of at least 85%, or at least 90%. The amount of unreacted monomer can be held to about 15% or less, or about 10% or less, or about 5% or less. The reaction time can be held to less than 8 h, or less than 6 h, or 4 h or less.

For example, tributylmagnesium ate complex can be successfully used in magnesium halogen exchange of aryl and heteroaryl monomers listed in Table 1. Magnesium-halogen exchange reactions via organomagnesium ate complexes have been published by Oshima, in the benzene, pyridine and thiophene series. [(1) Kitagawa et al. *Angew. Chem., Int. Ed.* 2000, 39, 2481-2483 (2) Inoue et al. *J. Org. Chem.* 2001, 66, 4333-4339]

In the representation $R^1(MgX)_n$·LiY for the organomagnesium reagent, the metal activation agent can be the LiY component.

In general, lithium salt is a preferred embodiment compared to magnesium and zinc salt.

Combining Step

The unsaturated ring compound and the organomagnesium reagent can be combined under conditions which facilitate the metal halogen exchange. Conditions include temperature, pressure, solvent, mixing, amounts, time, light, and the like, as known in the art of organic synthesis and polymer chemistry. Comparative testing can be carried out to determine the degree of activation by the metal activation agent, and which conditions promote the activation the most.

In the combining step, solvents can be used which are compatible with the metal-halogen exchange reaction.

For example, the amounts of the unsaturated ring compound and the organomagnesium reagent can be characterized by a molar ratio which can be for example about 0.8:1 to about 1.2:1, or about 0.9:1 to about 1.1:1, or about 1:1. The ratio can be adapted to provide for formation of a second compound which is a mono-Grignard reagent, wherein only one of the halogens has undergone metal halogen exchange. The amount of di- or bis-Grignard can be negligible or substantially zero.

The combining step can be carried out at a temperature between for example about −78° C. to about 80° C., or about 15° C. and about 80° C., or up to reflux temperatures of solvent used. One skilled in the art can examine temperature to see if other temperatures can be used including low temperatures such as for example −78° C. to 25° C., or −50° C. to 25° C. For example, one reason to use lower temperatures would be if other functional groups are present which may be temperature sensitive.

The second compound can be formed in the reaction mixture in the combining step in yield of at least about 80%, or at least about 90%, or at least about 95%, or at least about 98%, up to substantially a 100% yield so that a substantially complete conversion can be achieved.

If desired, reaction can be adapted to form gaseous by-products such as methyl bromide.

The Second Compound

The second compound is formed and can then for example function as a polymerization monomer. It can be a mono-Grignard reagent. It can couple with itself to form oligomers and/or polymers. One of the halogen sites, which has undergone metal-halogen exchange, can be a nucleophilic site, whereas the other halogen can be an electrophilic site. The coupling can provide for carbon-carbon bond formation.

Coupling Step

By carbon-carbon bond formation, higher molecular weight structures can be built including oligomers and polymers. Coupling, oligomerization, or polymerization conditions can be varied to induce reaction as known in the art of polymer chemistry including for example temperature, pressure, catalyst or initiator, amounts, pressure, mixing, sonication, microwaves, quenching, and the like.

Figure 7:
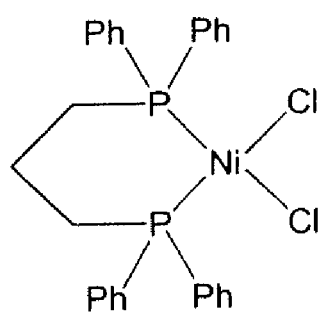
FIG. 7 illustrates nickel complexes for coupling step.
Figure 7:
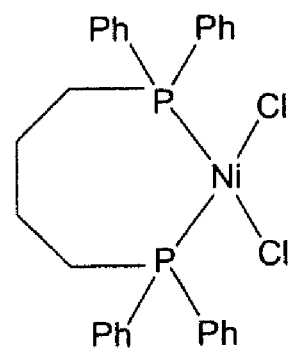

Coupling can be carried out in the presence of a transition metal complex which can function as a catalyst or an initiator. The transition metal can be for example nickel, palladium, or platinum. Kumada coupling can be used. In particular, nickel complexes can be used including for example nickel with ligand or chelating complexes such as for example nickel phosphine complexes. Examples of ligands include phosphines, fluorophosphines, and diimines. Two examples for transition metal complexes are given in FIG. 7. Another example of a transition metal complex is Ni(II)—diimine complexes such as ArN=C(An)—C(An)=NAr)$NiBr_2$ wherein Ar can be for example 2-t-$BuC_6H_4$ and An can be a fused aromatic group as describe in for example Killian et al, J. Am. Chem. Soc., 1996, 118, 11664.

In order for Kumada coupling to be effective, excess unreacted magnesium metal can be and should be removed.

Coupling can be carried out at for example a temperature of about 15° C. to about 70° C.

The coupling step can provide upon isolation of the oligomer or polymer a polymerization yield of at least 50%, or at least 60%, or at least 70%, or at least 80%, or at least 90%.

Reactions can be facilitated by microwaves as described in for example Carter et al., Macromolecules, 2002, 35, 6757-6759.

While the present invention is not limited by theory, principles of the chain growth mechanism and cross-coupling polymerization are described in for example Sheina et al., Macromolecules, 2004, 37, 3526-3528; Iovu et al., Polymer Preprints, 2005, 46(1), 660-661.

Characterization

The product of coupling can be a conjugated polymer or oligomer. The conjugated polymer or oligomer can be a soluble polymer or oligomer, including soluble in water or non-aqueous solvent including organic solvents like ethers, alcohols, alkanes, and esters.

The oligomer or polymer can be isolated and purified by methods known in the art including precipitation and extraction including soxhlett extraction. In many applications, it is important to remove metals including the magnesium as well as the transition metal such as nickel used in coupling. Metal impurities can be reduced to below for example 100 ppm for each metal and below 100 ppm for all metals combined.

The number average molecular weight of the coupled product can be for example at least 5,000, or at least 10,000, or at least 15,000 as measured by GPC methods using polystyrene standards. Number average molecular weight can be for example 5,000 to 500,000, or 5,000 to 50,000. The polydispersity, as measured by for example GPC, can be for example less than about 3, or less than about 2.5, or less than about 2, including for example 1.1 to about 2.5, or about 1.1 to about 2.0.

Polymer end groups can be characterized by for example MALDI-TOF MS analysis. Polymer end groups can be for example H/X, H/H, X/R, and H/R, wherein X is a halogen such as bromine, and R is an alkyl group such as isopropyl. See for example Liu et al., Macromolecules, 1999, 32, 5777-5785.

Copolymers Including Segmented, Alternating, and Block Copolymers

Block copolymers can be prepared as described in for example U.S. Pat. No. 6,602,974 to McCullough et al including polythiophene block copolymers. AB and ABA types can be prepared.

Blends

The oligomers and polymers provided herein can be further combined with other oligomers and polymers to form blends.

Applications and Devices

The oligomers and polymers provided herein can be used as or in compositions which function in devices as for example light emitting materials, hole injection, or hole transport layers. Thin films can be formed by spin coating or drop casting or blading methods. Multilayer structures can be built. Conducting polymers produced as described herein can be doped to control conductivity in the conductor, semiconductor space as needed. Applications can be executed in solution or solid state.

One application area is light emission, LEDs, light emitting polymers, electroluminescence, photoluminescence, OLEDs, PLEDs, and in particular blue light emission as described in for example Marsitzky et al., Adv. Mater., 2001, 13, No. 14, Jul. 18, 2001. See also, Li et al., Chem. Mater., 2004, 16, 2165-2173; Pasini et al., J. Mater. Chem., 2003, 13, 807-813; Pei et al., J. Am. Chem. Soc., 1996, 118, 7416-7417; Ranger et al., Macromolecules, 1997, 30, 7686-7691; Liu et al., Macromolecules, 2000, 33, 8945-8952; Herguth et al., Macromolecules, 2002, 35, 6094-6100; Peng et al., Macromolecules, 2005, 38, 7292-7298.

Additional applications and devices can be found in Plextronics patent applications and publications including for example (i) 2006/0078761 published Apr. 13, 2006 (electroluminescent devices); (ii) 2006/0076050 published Apr. 13, 2006 (photovoltaic devices), and (iii) 2006/0175582 published Aug. 10, 2006 (hole injection and transport layers).

Devices can be built comprising electrodes, active layers, and intermediate layers between active layers and electrodes.

Field effect transistor and emitter applications are described in for example Hwang et al., Chem. Mater., 2004, 16, 1298-1303.

Variable band gap systems and applications are described in Tsuie et al, J. Mater. Chem., 1999, 9, 2189-2200.

Other applications for conjugated polymers including polyfluorenes, and various derivatives thereof, are described in for example U.S. Pat. No. 5,777,070 to Inbasekaran et al (Dow Chemical); U.S. Pat. No. 5,900,327 to Pei et al. (Uniax); U.S. Pat. No. 5,962,631 to Woo et al. (Dow Chemical); U.S. Pat. No. 6,362,310 to Woo et al., (Dow Chemical); U.S. Pat. No. 6,777,531 to Yasuda et al. (Sony International).

If desired, polymers can be patterned or printed by for example lithography, see for example Zhai et al., Langmuir, 2003, 19, 6492-6497.

Water soluble polymers, based on pendant carboxylic acid functionality, and applications in chromatic chemosensing are described in for example Ewbank et al., Tetrahedron, 60 (2004), 11269-11275.

In some applications, conducting polymers can be combined with nanoparticles, including gold and metal nanoparticles, in applications, as described in for example, Zhai et al., J. Mater. Chem., 2004, 14, 141-143.

Following synthesis, polymers can be further functionalized for a particular application as described in for example Zhai et al., Macromolecules, 2003, 36, 61-64, including for example carboxylic acid, amino, and thiol functionalization.

Other application areas include for example optical, electronic, optoelectronic, sensors, chemical and optical sensors, printable electronics, thin film transistors, polymer transistors, photovoltaic and solar cells, electrostatic dissipation coatings, and plastic lasers.

WORKING EXAMPLES

Additional description is provided with use of non-limiting working examples.

Working Example 1A—Polyfluorene

Synthesis of iPrMgCl.LiCl complex was achieved by two methods. The first method is based on the reaction of iPrMgCl with LiCl in THF, while the second method uses the preparation of the Grignard reagent from i-propyl chloride and magnesium in the presence of LiCl.

Synthesis of iPrMgCl.LiCl from iPrMgCl and LiCl.

A dry 25 mL three-neck flask was flashed with nitrogen and was charged with a 2M solution of iPrMgCl in THF (2.5 mL, 5 mmol) and 2.5 mL of anhydrous THF. LiCl (0.22 g, 5 mmol) was added to the reaction flask under nitrogen. The reaction mixture was stirred for 8-12 hrs at 40° C., until the complete consumption of the LiCl salt.

Synthesis of of iPrMgCl.LiCl from iPrCl, Mg and LiCl.

Magnesium turnings (2.67 g, 110 mmol) and anhydrous LiCl (4.24 g, 100 mmol) were placed in a nitrogen flushed flask, and anhydrous THF (50 mL) was added. A solution of iPrCl (9.1 mL, 100 mmol) in anhydrous THF (50 mL) was slowly added at room temperature. After the addition, the reaction mixture was stirred for 12 hrs at room temperature. The gray solution of iPrMgCl.LiCl was cannulated under nitrogen in another flask and removed the unreacted magnesium. The iPrMgCl.LiCl complex was obtained in a yield of 98%. The concentration of iPrMgCl.LiCl was determined (about 1M). Increasing the reaction temperature resulted in faster metal halogen exchange.

Lithium t-butoxide was also successfully used as a metal activation agent.

The use of t-butyl magnesium chloride-lithium chloride complex resulted in a very slow metal halogen exchange process. Addition of 15-c-5 crown ether as additive increased the rate of magnesium halogen exchange.

General procedure for the synthesis of poly(9,9-dioctylfluorene) using iPrMgCl.LiCl.

Figure 3:
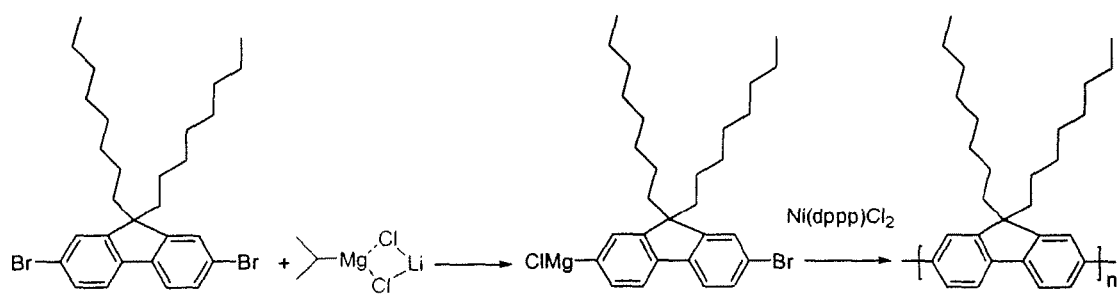
FIG. 3 illustrates polymerization of 9,9-dioctyl-2,7-dibromofluorene.

A dry 50 mL three-neck flask was flashed with nitrogen and was charged with a 1 M solution of iPrMgCl.LiCl in THF (5 mL, 5 mmol). A solution of 9,9-dioctyl-2,7-dibromofluorene (2.74 g, 5 mmol) in 5 mL of anhydrous THF was added under nitrogen. The reaction mixture was stirred for 8-12 hrs at 40° C. At this time an aliquot was collected and quenched with methanol. GC-MS analysis of this reaction mixture confirmed the formation of monoGrignard reagent in 95-99% yield. The reaction mixture was allowed to cool down to room temperature, at which time Ni(dppp)Cl$_2$ (0.02 g, 0.04 mmol) was added to the reaction mixture. The polymerization was allowed to proceed for 20 min at room temperature followed by quenching of the reaction mixture with methanol. The precipitated yellow-green polymer was filtered through a thimble and subjected to methanol extraction. The polymer was dried under vacuum for 12 hrs. The yield of polymerization was 60% (1.2 g). Polymer with $M_n$=14000 and PDI=1.7 was obtained. The polymer contained H/Br, H/H, Br/isopropyl and H/isopropyl end-groups as determined from MALDI-TOF MS analysis FIG. 3 provides a schematic on the synthesis of poly(9,9-dioctyl-2,7-dibromofluorene).

Working Example 1B

Synthesis of Ate Complex n-Bu$_3$MgLi

Figure 9:
FIG. 9 illustrates the synthesis of lithium tributylmagnesate from n-BuLi and n-BuMgCl.

Butyl lithium (1.6 M in hexanes, 1.1 mmol) was added to a solution of BuMgCl (2M in THF, 0.55 mmol) in dry toluene (2 mL) at −10° C., under nitrogen. After stirring for 1 h at −10° C., a solution of aryl or heteroaryl halide monomer (1.65 mmol in 5 mL dry THF) was added under nitrogen. FIG. 9 provides a schematic of the synthesis of lithium tributylmagnesate from n-BuLi and n-BuMgCl.

General procedure for the synthesis of poly(9,9-dioctylfluorene) using n-Bu$_3$MgLi.

Figure 10:
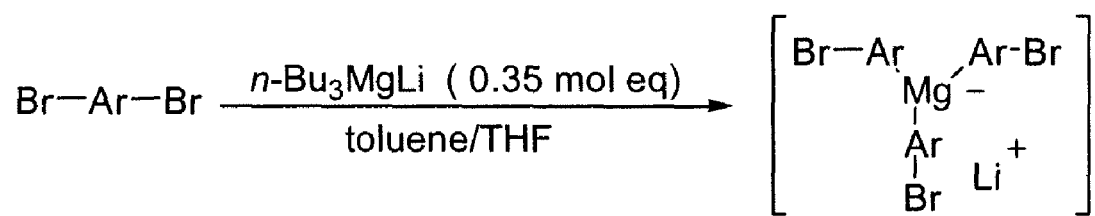
FIG. 10 illustrates magnesium halogen exchange with lithium tributylmagnesate (n-Bu$_3$MgLi).
Figure 11:
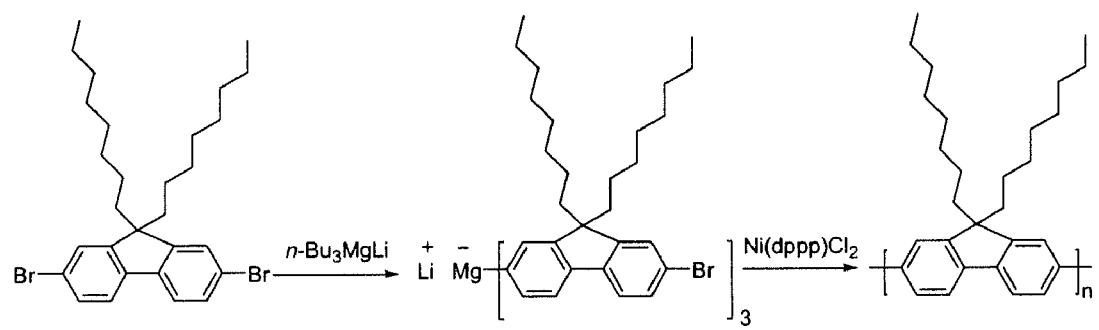
FIG. 11 illustrates the synthesis of poly(9,9-dioctyl fluorine) using magnesium ate complex for magnesium halogen exchange.
Figure 12:
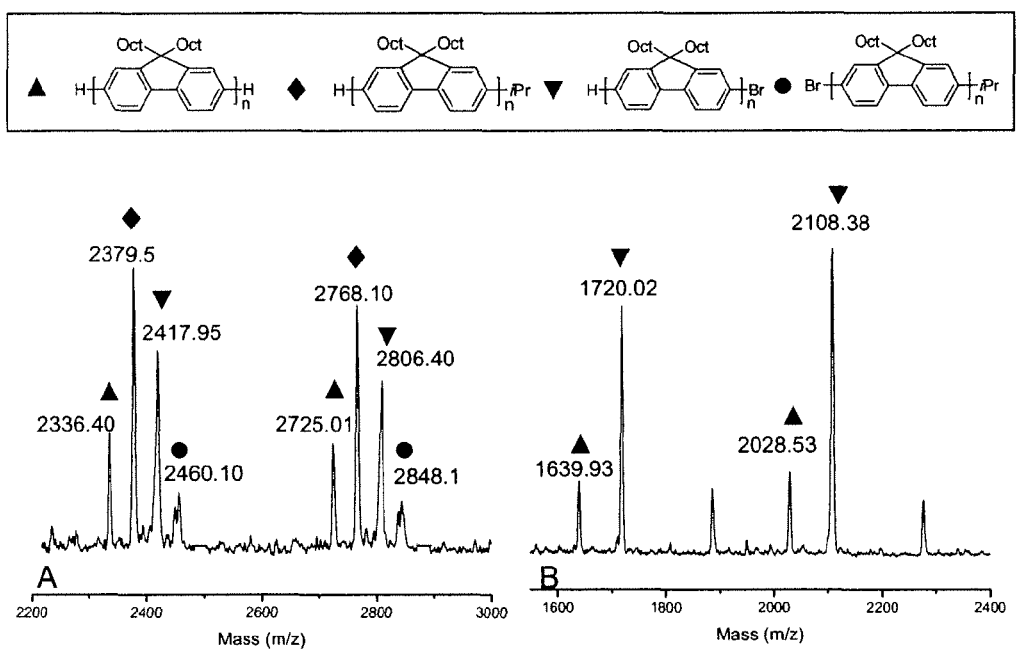
FIG. 12 illustrates MALDI-TOF MS spectra of poly(9,9-dioctylfluorene): A-polymer synthesized with iPrMgCl.LiCl; B-polymer synthesized with tBuMgCl.LiCl.15-c-5.

A dry 25 mL three-neck flask was flushed with nitrogen and was charged with butyl lithium (1.6 M in hexanes, 1.1 mmol) and a solution of BuMgCl (2M in THF, 0.55 mmol) in dry toluene (2 mL) at −10° C. After stirring for 1 h at −10° C., a solution of of 9,9-dioctyl-2,7-dibromofluorene (0.9 g, 1.65 mmol) in 5 mL of anhydrous THF was added under nitrogen. The reaction mixture was stirred for 4 hrs at 40° C. At this time an aliquot was collected and quenched with methanol. GC-MS analysis of this reaction mixture confirmed the formation of monoGrignard reagent in 90% yield. The reaction mixture was allowed to cool down to room temperature, at which time Ni(dppp)Cl$_2$ (0.01 g, 0.02 mmol) was added to the reaction mixture. The polymerization was allowed to proceed for 20 min at room temperature followed by quenching of the reaction mixture with methanol. The precipitated yellow-green polymer was filtered through a thimble and subjected to methanol extraction. The polymer was dried under vacuum for 12 hrs. The yield of polymerization was 60%. Polymer with $M_n$=10000 and PDI=1.55 was obtained. The polymer contained H/Br, H/H, Br/butyl and H/butyl end-groups as determined from MALDI-TOF MS analysis. FIG. 10 provides a schematic of magnesium halogen exchange with lithium tributylmagnesate (n-Bu$_3$MgLi). FIG. 11 provides a schematic of the synthesis of poly(9,9-dioctyl fluorine) using magnesium ate complex for magnesium halogen exchange. FIG. 12 illustrates MALDI-TOF MS spectra of poly(9,9-dioctylfluorene): A-polymer synthesized with iPrMgCl.LiCl; B-polymer synthesized with tBuMgCl.LiCl.15-c-5.

Working Example 2—Polypyrrole

Synthesis of iPrMgCl.LiCl from iPrMgCl and LiCl.

A dry 25 mL three-neck flask was flashed with nitrogen and was charged with a 2M solution of iPrMgCl in THF (2.5 mL, 5 mmol) and 2.5 mL of anhydrous THF. LiCl (0.22 g, 5 mmol) was added to the reaction flask under nitrogen. The reaction mixture was stirred for 8-12 hrs at 40° C., until the complete consumption of the LiCl salt.

Synthesis of of iPrMgCl.LiCl from iPrCl, Mg and LiCl.

Magnesium turnings (2.67 g, 110 mmol) and anhydrous LiCl (4.24 g, 100 mmol) were placed in a nitrogen flushed flask, and anhydrous THF (50 mL) was added. A solution of iPrCl (9.1 mL, 100 mmol) in anhydrous THF (50 mL) was slowly added at room temperature. After the addition, the reaction mixture was stirred for 12 hrs at room temperature. The gray solution of iPrMgCl.LiCl was cannulated under nitrogen in another flask and removed the unreacted magnesium. The iPrMgCl.LiCl complex was obtained in a yield of 98%. The concentration of iPrMgCl.LiCl was determined (about 1M).

General procedure for the synthesis of poly(N-dodecyl pyrrole).

Figure 4:
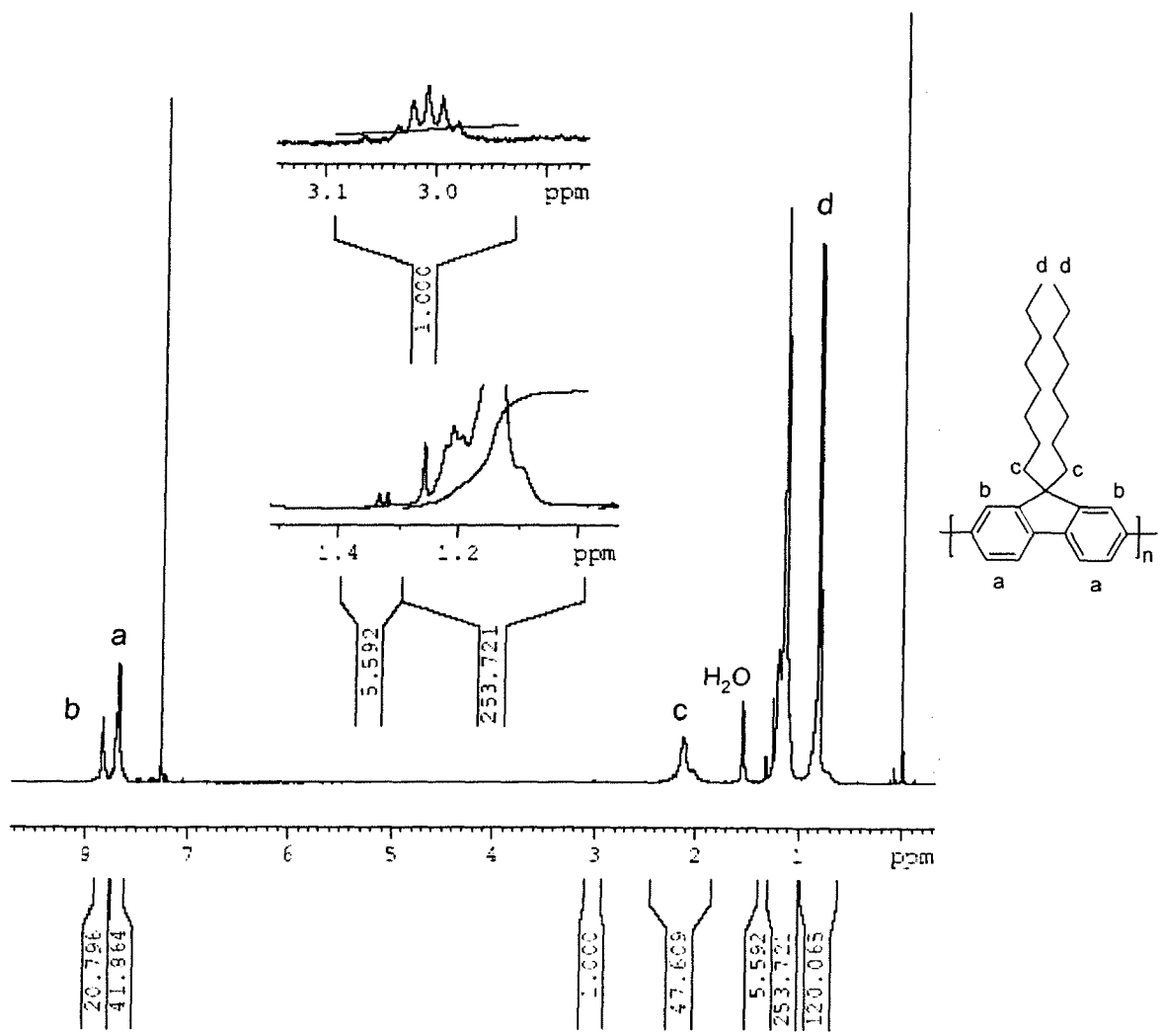
FIG. 4 provides an $^1$H NMR of poly(9,9-dioctylfluorene) synthesized by GRIM with iPrMgCl—LiCl and Ni(dpp)Cl$_2$ catalyst.
Figure 5:
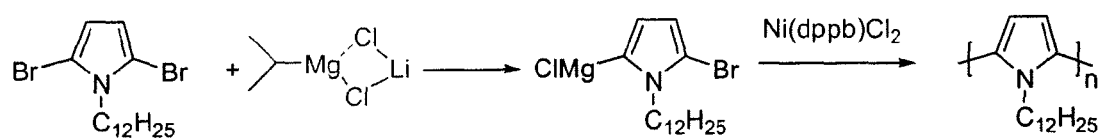
FIG. 5 illustrates polymerization of 2,5-dibromo-N-dodecyl pyrrole.
Figure 6:
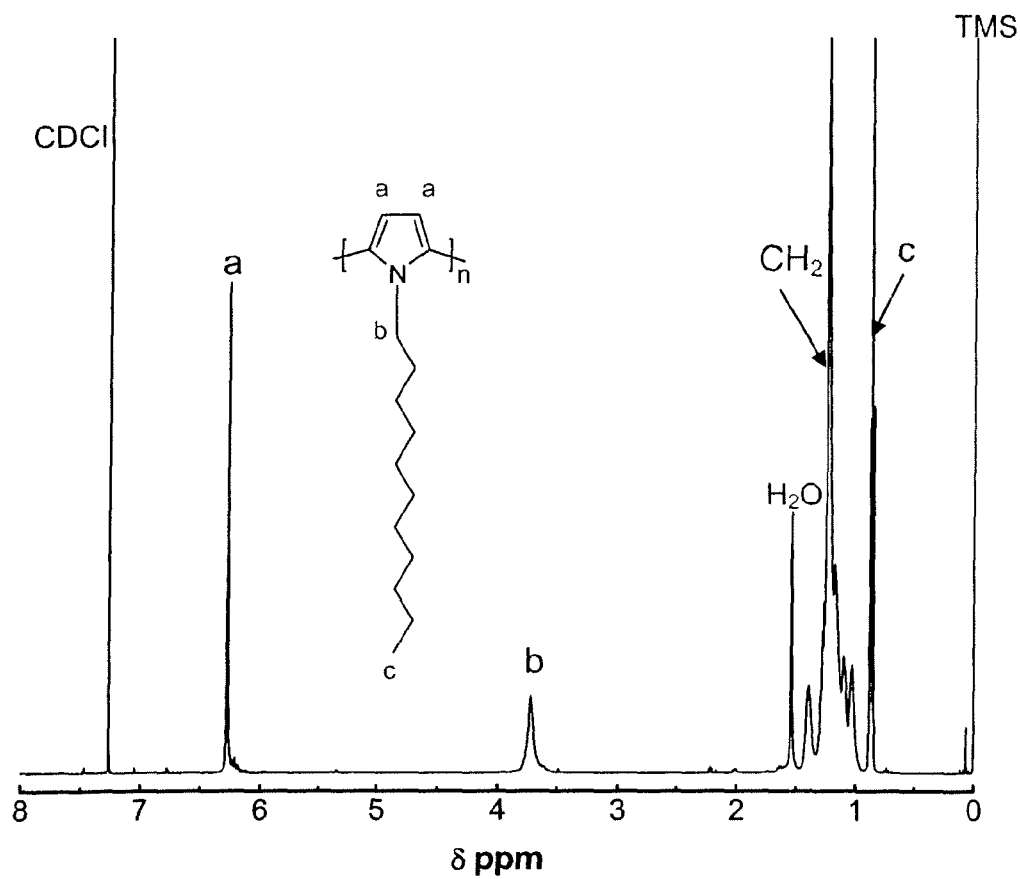
FIG. 6 provides an $^1$H NMR of poly(N-dodecyl pyrrole).

A dry 50 mL three-neck flask was flashed with nitrogen and was charged with a 1 M solution of iPrMgCl.LiCl in THF (5 mL, 5 mmol). A solution of 2,5-dibromo-N-dodecyl pyrrole (1.96 g, 5 mmol) in 5 mL of anhydrous THF was added under nitrogen. The reaction mixture was stirred for 1 hr at room temperature. At this time an aliquot was collected and quenched with methanol. GC-MS analysis of this reaction mixture confirmed the formation of monoGrignard reagent in 98-99% yield. At this time Ni(dppb)Cl$_2$ (0.022 g, 0.04 mmol) was added to the reaction mixture. The polymerization was allowed to proceed for 48 hrs at 50° C. followed by quenching of the reaction mixture with methanol. The precipitated green polymer was filtered through a thimble and subjected to methanol extraction. The polymer was dried under vacuum for 12 hrs. The yield of polymerization was 50% (0.58 g). Polymer with $M_n$=11900 and PDI=1.4 was obtained. FIG. 4 provides a schematic of synthesized of poly(2,5-dibromo-N-dodecyl pyrrole) using GRIM with iPrMgCl-LiCl and Ni(dpp)Cl$_2$ catalyst. FIG. 5 illustrates the polymerization process of 2,5-dibromo-N-dodecyl pyrrole. FIG. 6 provides an $^1$H NMR of poly(N-dodecyl pyrrole).

Comparative Example

Magnesium halogen exchange of 9,9-dioctyl-2,7-dibromofluorene with isopropyl magnesium chloride or t-butyl magnesium chloride was unsuccessful, less than 5% monomer reacted after 24 h at 40° C.

Additional Data

Tables 2 and 3 provide experimental comparisons between different organomagnesium reagents used in magnesium halogen exchange and GRIM polymerization, respectively, for synthesizing 9,9-dioctyl-2,7-dibromofluorene.

TABLE 2

Experimental results for magnesium halogen exchange of 9,9-dioctyl-2,7-dibromofluorene

| Reagent | Reaction Time (h) | Mono- | Di- | Unreacted monomer |
|---|---|---|---|---|
| iPrMgCl | 24 | 2 | 0 | 98 |
| iPrMgCl•LiCl | 12 | 85 | 0 | 15 |
| iPrMgCl•LiOtBu | 8 | 90 | 7 | 3 |
| tBuMgCl•LiCl[a] | 12 | 85 | 0 | 15 |
| Bu$_3$MgLi[b] | 4 | 90 | 9 | 1 |

[a]15-c-5 used as additive; [t-BuMgCl]:[LiCl]:[15-c-5] = 1:1:1
[b][Bu$_3$MgLi]:[DODBF] = 0.35:1

TABLE 3

Experimental results for GRIM polymerization of 9,9-dioctyl-2,7-dibromofluorene

| Polymer | Conversion (%) | $M_n$ (GPC) | PDI (GPC) | $\lambda_{max}$ (nm) |
|---|---|---|---|---|
| P1[a] | 88 | 14970 | 1.45 | 388 |
| P2[b] | 74 | 5800 | 1.66 | 380 |

TABLE 3-continued

Experimental results for GRIM polymerization of 9,9-dioctyl-2,7-dibromofluorene

| Polymer | Conversion (%) | $M_n$ (GPC) | PDI (GPC) | $\lambda_{max}$ (nm) |
|---------|---------------|-------------|-----------|----------------------|
| P3[c]   | 85            | 29000       | 1.50      | 390                  |
| P4[d]   | 92            | 9650        | 1.55      | 384                  |

[a]iPrMgCl•LiCl; [M]$_0$/[Ni] = 100, [M]$_0$ = 0.2 mol/L, Temp. = 23° C.
[b]iPrMgCl•LiOtBu, [M]$_0$/[Ni] = 100, [M]$_0$ = 0.2 mol/L, Temp. = 23° C.
[c]tBuMgCl•LiCl•15-c-5, [M]$_0$/[Ni] = 50, [M]$_0$ = 0.2 mol/L, Temp. = 23° C.
[d]Bu$_3$MgLi, [M]$_0$/[Ni] = 50, [M]$_0$ = 0.2 mol/L, Temp. = 23° C.

Working Example 3—Polycarbazole

Figure 13:
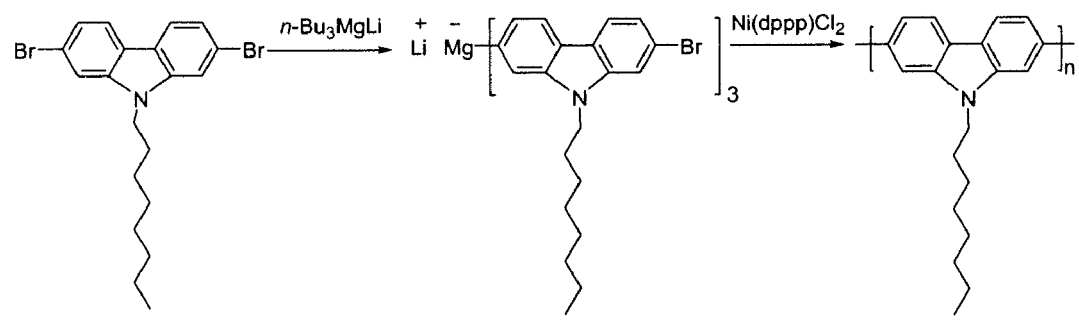
FIG. 13 illustrates synthesis of poly(N-octy-2,7-carbazole) using magnesium ate complex for magnesium halogen exchange.

Magnesium halogen exchange with i-PrMgCl-LiCl of 2,7-dibromo-N-octyl carbazole was relatively slow and the reaction did not go to completion. In contrast, when lithium tributylmagnesate (n-Bu$_3$MgLi) was used for magnesium halogen exchange the reaction was completed in 5 hours at room temperature. Synthesis of poly(N-octyl-2,7-carbazole) is shown in FIG. 13.

General procedure for the synthesis of poly(N-octyl-2,7-carbazole).

A dry 25 mL three-neck flask was flushed with nitrogen and was charged with butyl lithium (1.6 M in hexanes, 1.1 mmol) and a solution of BuMgCl (2M in THF, 0.55 mmol) in dry toluene (2 mL) at −10° C. After stirring for 1 h at −10° C., a solution of of 2,7-dibromo N-octyl carbazole (0.7 g, 1.65 mmol) in 5 mL of anhydrous THF was added under nitrogen. The reaction mixture was stirred for 5 hrs at room temperature. At this time an aliquot was collected and quenched with methanol. GC-MS analysis of this reaction mixture confirmed the formation of monoGrignard reagent in 80% yield. Di-Grignard reagent was formed in 20% yield. Ni(dppp)Cl$_2$ (0.01 g, 0.02 mmol) was added to the reaction mixture. The polymerization was allowed to proceed for 4 h at room temperature followed by quenching of the reaction mixture with methanol. The precipitated polymer was filtered through a thimble and subjected to methanol extraction. The polymer was dried under vacuum for 12 hrs. The yield of polymerization was 50%. Polymer with $M_n$=2600 and PDI=1.23 was obtained.

Working Example 4—Polyhenylene

General Procedure for the Synthesis of poly(2,5-dioctyloxy-p-phenylene)

Figure 14:
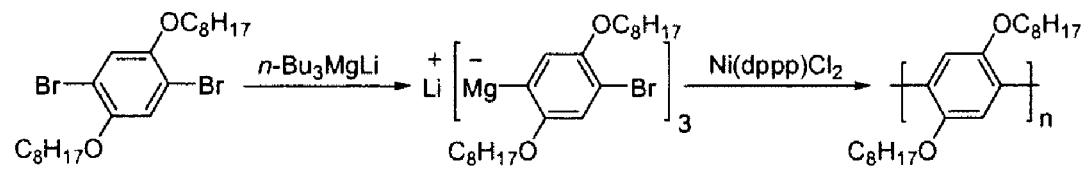
FIG. 14 illustrates synthesis of poly(2,5-dioctyloxy-p-phenylene) using magnesium ate complex for magnesium halogen exchange.

A dry 25 mL three-neck flask was flushed with nitrogen and was charged with butyl lithium (1.6 M in hexanes, 1.1 mmol) and a solution of BuMgCl (2M in THF, 0.55 mmol) in dry toluene (2 mL) at −10° C. After stirring for 1 h at −10° C., a solution of of 1,4-dibromo-2,5-dioctyloxybenzene (0.81 g, 1.65 mmol) in 5 mL of anhydrous THF was added under nitrogen. The reaction mixture was stirred for 5 hrs at 40° C. At this time an aliquot was collected and quenched with methanol. GC-MS analysis of this reaction mixture confirmed the formation of monoGrignard reagent in 80% yield. Ni(dppp)Cl$_2$ (0.01 g, 0.02 mmol) was added to the reaction mixture. The polymerization was allowed to proceed for 6 h at room temperature followed by quenching of the reaction mixture with methanol. The precipitated white polymer was filtered through a thimble and subjected to washing with cold methanol. The polymer was dried under vacuum for 12 hrs. The yield of polymerization was 50%. Polymer with $M_n$=3600 and PDI=1.33 was obtained. FIG. 14 shows the synthesis of poly(2,5-dioctyloxy-p-phenylene).

Priority provisional application 60/841,548 includes the following 63 embodiments:

1. A method comprising:
   providing an unsaturated ring compound comprising at least two halogen ring substituents,
   providing an organomagnesium reagent comprising an organomagnesium component and a metal activation agent,
   combining the unsaturated ring compound with the reagent to form a second compound by metal-halogen exchange, wherein the metal activation agent activates the metal-halogen exchange,
   coupling the second compound to itself in an oligomerization or polymerization reaction.
2. The method according to 1, wherein the unsaturated ring compound comprises at least one aromatic or pseudo-aromatic ring.
3. The method according to 1, wherein the unsaturated ring compound comprises one or two rings, wherein the rings are five or six membered rings.
4. The method according to 1, wherein the unsaturated ring compound is a heterocyclic ring compound.
5. The method according to 1, wherein the unsaturated ring compound is a non-heterocyclic ring compound.
6. The method according to 1, wherein the unsaturated ring compound comprises a single heterocyclic ring, a single aromatic ring, or a single bi-phenyl ring system.
7. The method according to 1, wherein the unsaturated ring compound is a thiophene compound, a pyrrole compound, or a fluorene compound.
8. The method according to 1, wherein the unsaturated ring compound comprises an alkyl, aryl, or alkoxy ring substituent.
9. The method according to 1, wherein the unsaturated ring compound comprises two halogen atoms which are bonded to carbon ring atoms which are not adjacent to each other and are separated by a heterocyclic atom.
10. The method according to 1, wherein the unsaturated ring compound comprises two rings, wherein each ring comprises a halogen ring substituent.
11. The method according to 1, wherein the halogen is bromine.
12. The method according to 1, wherein the organomagnesium reagent is prepared by combining an alkyl magnesium halide with a lithium salt.
13. The method according to 1, wherein the organomagnesium reagent is prepared by combining an alkyl halide, magnesium, and a lithium salt.
14. The method according to 1, wherein the organomagnesium reagent is represented by R$^1$(MgX)$_n$.LiY, wherein:
   n is 1 or 2;
   R$^1$ is a substituted or unsubstituted C4-C24 aryl or C3-C24 heteroaryl, containing one or more heteroatoms as B, O, N, S, Se, P, F, Cl, Br, I, or Si; linear or branched, substituted or unsubstituted C1-C20 alkyl, C2-C20 alkenyl or C2-C20 alkinyl; or substituted or unsubstituted C3-C20 cycloalkyl; or a derivative thereof;
   X and Y are independently or both Cl, Br or I, preferably Cl; HalO$_n$ (where n=3, 4); carboxylate of formula RCO$_2$; alkoxide or phenoxide of formula RO; dialkoxide of formula LiO—R—O; disilazide of formula (R$_3$Si)$_2$N; thiolate of formula SR; RP(O)O$_2$; or SCOR; where R is defined as R$^1$ above;
   linear or branched, substituted or unsubstituted C1-C20 alkyl or C3-C20 cycloalkyl amine of formula RNH; dialkyl/arylamine of formula R$_2$N (where R is defined as above or R$_2$N represents a heterocyclic alkylamine); phosphine of formula PR$_2$ (where R is defined as above or PR2 represents a heterocyclic phosphine); O$_n$SR (where n=2 or 3 and R is defined as above); or NO$_n$ (where n=2 or 3); or X=R$^1$ as defined above; and a derivative thereof.

15. The method according to 1, wherein the metal activation agent comprises lithium, magnesium, potassium, or zinc.
16. The method according to 1, wherein the metal activation agent comprises lithium.
17. The method according to 1, wherein the metal activation agent comprises a lithium salt.
18. The method according to 1, wherein the organomagnesium component comprises an aryl or alkyl magnesium reagent.
19. The method according to 1, wherein an additive is further present in the combining step comprising a polyether, a polyamine, or a crown ether.
20. The method according to 1, wherein the combining step is carried out at a temperature of about 15° C. and about 80° C.
21. The method according to 1, wherein the combining step is carried out using a molar ratio between unsaturated ring compound and organomagnesium reagent which is about 0.8:1 to about 1.2:1.
22. The method according to 1, wherein the second compound is formed in a reaction mixture in a yield of at least about 80%.
23. The method according to 1, wherein the second compound is formed in a reaction mixture in a yield of at least about 95%.
24. The method according to 1, wherein the coupling step comprises coupling the second compound in the presence of a transition metal complex.
25. The method according to 1, wherein the coupling step comprises coupling the second compound in the presence of a nickel complex.
26. The method according to 1, wherein the coupling step is carried out at a temperature of about 15° C. to about 70° C.
27. The method according to 1, wherein the coupling step provides upon isolation of the oligomer or polymer a polymerization yield of at least 50%.
28. The method according to 1, wherein the coupling step provides a polymer having upon isolation a number average molecular weight of at least 5,000.
29. The method according to 1, wherein the coupling step produces a conjugated polymer or oligomer.
30. The method according to 1, wherein the coupling step produces a conjugated polymer or oligomer which is soluble in water or non-aqueous solvent.
31. A method comprising:
    providing an unsaturated ring compound comprising at least two halogen ring substituents,
    providing a reagent represented by R$^1$(MgX)$_n$·LiY,
    combining the unsaturated ring compound with the reagent to form a second compound,
    polymerizing the second compound, wherein for the reagent:
    n is 1 or 2;
    R$^1$ is a substituted or unsubstituted C4-C24 aryl or C3-C24 heteroaryl, containing one or more heteroatoms as B, O, N, S, Se, P, F, Cl, Br, I, or Si; linear or branched, substituted or unsubstituted C1-C20 alkyl, C2-C20 alkenyl or C2-C20 alkinyl; or substituted or unsubstituted C3-C20 cycloalkyl; or a derivative thereof;
    X and Y are independently or both Cl, Br or I, preferably Cl; HalOn (where n=3, 4); carboxylate of formula RCO$_2$; alkoxide or phenoxide of formula RO; dialkoxide of formula LiO—R—O; disilazide of formula (R$_3$Si)$_2$N; thiolate of formula SR; RP(O)O$_2$; or SCOR; where R is defined as R$^1$ above;
    linear or branched, substituted or unsubstituted C1-C20 alkyl or C3-C20 cycloalkyl amine of formula RNH; dialkyl/arylamine of formula R$_2$N (where R is defined as above or R$_2$N represents a heterocyclic alkylamine); phosphine of formula PR$_2$ (where R is defined as above or PR2 represents a heterocyclic phosphine); OSR (where n=2 or 3 and R is defined as above); or NO$_n$ (where n=2 or 3); or X=R$^1$ as defined above; and a derivative thereof.

32. The method according to 31, wherein the unsaturated ring compound comprises at least one aromatic or pseudo-aromatic ring.
33. The method according to 31, wherein the unsaturated ring compound comprises one or two rings, wherein the rings are five or six membered rings.
34. The method according to 31, wherein the unsaturated ring compound is a heterocyclic ring compound.
35. The method according to 31, wherein the unsaturated ring compound is a non-heterocyclic ring compound.
36. The method according to 31, wherein the unsaturated ring compound comprises a single heterocyclic ring, a single aromatic ring, or a single bi-phenyl ring system.
37. The method according to 31, wherein the unsaturated ring compound is a thiophene compound, a pyrrole compound, or a fluorene compound.
38. The method according to 31, wherein the unsaturated ring compound comprises an alkyl, aryl, or alkoxy ring substituent.
39. The method according to 31, wherein the unsaturated ring compound comprises two halogen atoms which are bonded to carbon ring atoms which are not adjacent to each other.
40. The method according to 31, wherein the unsaturated ring compound comprises two halogen atoms which are bonded to carbon ring atoms which are not adjacent to each other and are separated by a heterocyclic atom.
41. The method according to 31, wherein the unsaturated ring compound comprises two rings, wherein each ring comprises a halogen ring substituent.
42. The method according to 31, wherein the halogen is bromine.
43. The method according to 31, wherein the reagent is (R$^1$)$_2$Mg LiY.
44. The method according to 31, wherein the reagent comprises R$^1$(MgX)n and LiY in a molar ratio of about 0.05 to about 6.0.
45. The method according to 31, wherein R$^1$ is an alkyl, and X and Y are halogen.
46. The method according to 31, wherein R$^1$ is a C3-C6 alkyl, and X and Y are chloro.
47. The method according to 31, wherein the reagent further comprises solvent and an additive.
48. The method according to 31, wherein the reagent is prepared by combining R$^1$(MgX)$_n$ and LiY.
49. The method according to 31, wherein the reagent is prepared by combining magnesium, R$^1$X, and LiY.
50. The method according to 31, wherein LiY is a lithium salt.
51. The method according to 31, wherein the combining step is carried out at a temperature of about 15° C. to about 80° C.
52. The method according to 31, wherein the combining step is carried out using a molar ratio between unsaturated ring compound and the reagent which is about 0.8:1 to about 1.2:1.

53. The method according to 31, wherein the second compound is formed in a reaction mixture in a yield of at least about 80%.
54. The method according to 31, wherein the second compound is formed in a reaction mixture in a yield of at least about 95%.
55. The method according to 31, wherein the coupling step comprises coupling the second compound in the presence of a transition metal complex.
56. The method according to 31, wherein the coupling step comprises coupling the second compound in the presence of a nickel complex.
57. The method according to 31, wherein the coupling step is carried out at a temperature of about 15° C. to about 70° C.
58. The method according to 31, wherein the coupling step provides upon isolation of the oligomer or polymer a polymerization yield of at least 50%.
59. The method according to 31, wherein the coupling step provides a polymer having upon isolation a number average molecular weight of at least 5,000.
60. The method according to 31, wherein the coupling step produces a conjugated polymer or oligomer.
61. A method comprising:
providing an unsaturated ring compound comprising at least two halogen ring substituents,
providing an organomagnesium reagent comprising an organic component, a magnesium component, and a metallic component comprising magnesium or a non-magnesium metal,
reacting the unsaturated ring compound with the organomagnesium reagent to form a second compound.
62. A method comprising:
providing an unsaturated ring compound comprising at least two halogen ring substituents,
providing an organomagnesium reagent comprising an organomagnesium component and a metal activation agent,
combining the unsaturated ring compound with the reagent to form a second compound by metal-halogen exchange, wherein the metal activation agent activates the metal-halogen exchange.
63. A method comprising:
providing a heterocyclic, aromatic, or biphenyl ring compound comprising two bromine ring substituents,
providing an organomagnesium reagent comprising an organomagnesium component and a lithium activation agent,
combining the ring compound with the organomagnesium reagent to form a second compound,
polymerizing the second compound with transition metal complex to form a conjugated polymer.

What is claimed is:
1. A method comprising:
providing an unsaturated ring compound comprising at least two halogen ring substituents, wherein the unsaturated ring compound is pyrrole, fluorene, carbazole or phenylene,
providing an organomagnesium reagent comprising an organomagnesium component and a metal activation agent,
combining the unsaturated ring compound with the reagent to form a second compound by metal-halogen exchange, wherein the metal activation agent activates the metal-halogen exchange,
reacting the second compound in a polymerization reaction to form a soluble conjugated polymer, wherein the reacting step provides a polymer having upon isolation a number average molecular weight of at least 5,000.

2. The method according to claim 1, wherein the unsaturated ring compound comprises an alkyl, aryl, or alkoxy ring substituent.
3. The method according to claim 1, wherein the unsaturated ring compound comprises two halogen atoms which are bonded to carbon ring atoms which are not adjacent to each other and are separated by a heterocyclic atom.
4. The method according to claim 1, wherein the unsaturated ring compound comprises two rings, wherein each ring comprises a halogen ring substituent.
5. The method according to 1, wherein the halogen is bromine.
6. The method according to claim 1, wherein the organomagnesium reagent is prepared by combining an alkyl magnesium halide with a lithium salt.
7. The method according to claim 1, wherein the organomagnesium reagent is prepared by combining an alkyl halide, magnesium, and a lithium salt.
8. The method according to claim 1, wherein the organomagnesium reagent is prepared by combining an alkyl magnesium halide with an alkyllithium compound.
9. The method according to claim 1, wherein the metal activation agent comprises lithium, magnesium, potassium, or zinc.
10. The method according to claim 1, wherein the metal activation agent comprises lithium.
11. The method according to claim 1, wherein the metal activation agent comprises a lithium salt or alkyllithium compound.
12. The method according to claim 1, wherein an additive is further present in the combining step comprising a polyether, a polyamine, or a crown ether.
13. The method according to claim 1, wherein the second compound is formed in a reaction mixture in a yield of at least about 95%.
14. The method according to claim 1, wherein the reacting step comprises reacting the second compound in the presence of a transition metal complex.
15. The method of claim 1, wherein the polymer is a homopolymer.
16. The method of claim 1, wherein the polymer is purified to have a metal impurity level of less than 100 ppm for all metals combined.
17. The method of claim 1, wherein the polymer is a polyfluorene and is purified to have a metal impurity level of less than 100 ppm for each metal.
18. The method of claim 1, wherein the unsaturated ring compound is a pyrrole compound.
19. The method of claim 1, wherein the unsaturated ring compound is

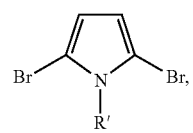

wherein R' is alkyl.
20. The method of claim 1, wherein the unsaturated ring compound is a fluorene compound.

21. The method of claim 1, wherein the unsaturated ring compound is

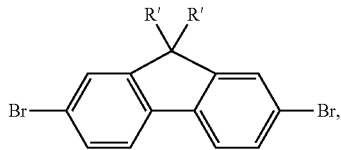

wherein R' is alkyl.

22. The method of claim 1, wherein the unsaturated ring compound is a carbazole compound.

23. The method of claim 1, wherein the unsaturated ring compound is

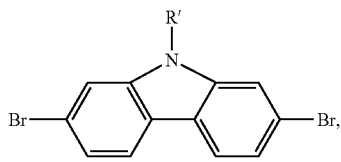

wherein R' is alkyl.

24. The method of claim 1, wherein the unsaturated ring compound is a phenylene compound.

25. The method of claim 1, wherein the unsaturated ring compound is

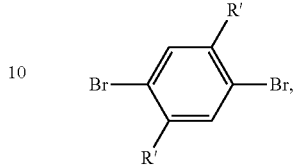

wherein R' is alkoxy.

26. The method of claim 1, wherein the organomagnesium reagent is selected from the group consisting of iPrMgCl.LiCl, iPrMgCl.LiOtBu, nBu$_3$MgLi and tBuMgCl.LiCl.

27. The method of claim 1, wherein the organomagnesium reagent is nBu$_3$MgLi.

* * * * *